United States Patent [19]

Suzuki et al.

[11] Patent Number: 4,877,726

[45] Date of Patent: Oct. 31, 1989

[54] METHOD FOR THE DETECTION OF ACUTE-PHASE TOXOPLASMA INFECTION

[75] Inventors: Yasuhiro Suzuki; Jack S. Remington, both of Menlo Park, Calif.; Georges Desmonts; Philippe Thulliez, both of Paris, France

[73] Assignee: Research Institute of Palo Alto Medical Foundation, Palo Alto, Calif.

[21] Appl. No.: 163,300

[22] Filed: Mar. 2, 1988

[51] Int. Cl.⁴ .................... G01N 33/569; C07K 15/04
[52] U.S. Cl. ......................................... 435/7; 436/507; 436/519; 436/811; 530/350; 530/403; 530/822
[58] Field of Search .................... 435/7; 436/507, 519, 436/811; 530/350, 403, 822

[56] References Cited

U.S. PATENT DOCUMENTS 4,361,647 11/1982 Remington .............................. 435/7
4,480,043 10/1984 Trouyez .......................... 435/947 X
4,609,630 9/1986 Yanovsky ............................ 436/519

OTHER PUBLICATIONS

*Infect. Immun.*, 41(2), 683–90, 1983, Erlich, H. et al., Identification of an Antigen–Specific Immunoglobulin M Antibody Associated with Acidic Toxoplasma Infection.

A Practical Manual of Medical & Biological Staining Techniques by Gurr, pp. 3–11, 1956, Interscience Publishers, Inc., N.Y.

*Primary Examiner*—Christine M. Nucker
*Attorney, Agent, or Firm*—Richard L. Neeley

[57] ABSTRACT

A method of detecting Toxoplasma infection and distinguishing acute infection from chronic infection is provided, comprising the steps of combining a sample suspected of containing antibodies to Toxoplasma antigens with a acute-phase-specific antigen reactive with an antibody specific for an acetone-treated Toxoplasma antigen under conditions favorable for formation of antigen-antibody complex, and detecting formation of the complex.

11 Claims, 2 Drawing Sheets

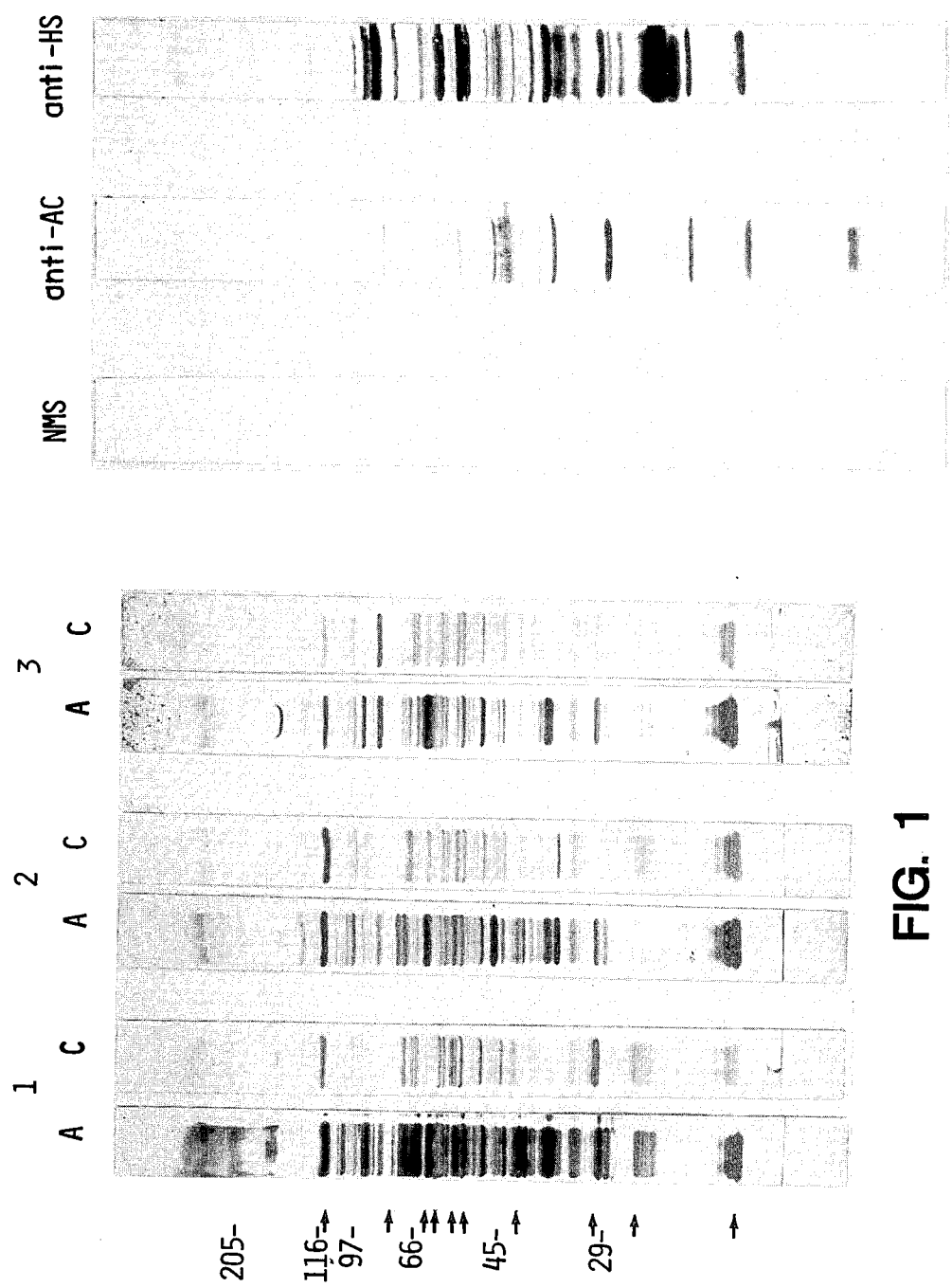

METHOD FOR THE DETECTION OF ACUTE-PHASE TOXOPLASMA INFECTION

BACKGROUND OF THE INVENTION

1. Field of the Invention

This invention relates to techniques for the detection of toxoplasma infections and is particularly directed to methods for distinguishing acute infection from chronic infection.

2. Description of the Background

The term toxoplasmosis refers to disease caused by the intracellular protozoan parasite *Toxoplasma gondii* and is differentiated from the more common, asymptomatic infection caused by this organism. *T. gondii* is a ubiquitous parasite that infects many different types of animals, including mammals and birds.

*T. gondii* is classified as a coccidian and exists in three forms: tachyzoite, cyst, and oocyst. Tachyzoites, found during acute infection, are the invasive form capable of initial infection and are capable of invading all mammalian cells except non-nucleated erythrocytes. Tissue cysts are formed within host cells after infection and contain multiple, up to thousands, of bradyzoites. Such cysts are the hallmark of chronic infection and are present for the life of the host. Cysts are important in transmission of infection, as they may be present in animal tissue ingested by carnivores. Oocysts represent a stage in sexual reproduction found only in the mucosal cells in the intestine of members of the cat family, from which they are subsequently excreted in the feces.

Transmission of infection to susceptible hosts occurs by ingestion of cysts or oocysts. Cysts are present in approximately 10% of lamb and 25% of pork used for human consumption. Direct contact with any material contaminated by infected cat feces may result in ingestion of oocysts, and this form can be transmitted to food by insects. Infections may also be acquired through blood or leukocyte transfusion, by organ transplatnation, or by transplacental transmission during pregnancy. Prevalence of infection in humans varies with locale and with eating and cooking habits. In the United States, approximately 5-30% of individuals 10 to 19 years old and 10-67% of individuals over 50 years old have serologic evidence of infection.

The immune response of the host primarily governs the outcome of acute infection. Both humoral and cell-mediated immunity are important. In immunecompromised individuals, the infection can be particularly severe. Toxoplasmic encephalitis is a major cause of morbidity and mortality in patients with acquired immunodeficiency syndrome (AIDS). Toxoplasma infection also has been estimated to be the cause of approximately 35% of cases of chorioretinitis in children and adults, usually as a consequence of congenital Toxoplasma infection acquired during pregnancy. Commonly, episodic flares of chorioretinitis cause destruction of irreplaceable retinal tissue and can lead to loss of vision.

Congenital transmission occurs from mothers who become infected during pregnancy. In the United States, approximately 80-90% of women in the child bearing age group are at risk. However, diagnosis of early acute-phase infection in the mother must be distinguished from chronic infection (which does not lead to transplacental infection of the fetus) because of side effects of existing treatments. For example, pyrimethamine is known to have the potential to cause birth defects.

The most widely used tests to establish the diagnosis of acute Toxoplasma infection are the Sabine-Feldman dye test, indirect fluorescent antibody (IFA) test, indirect hemagglutination (IHA) test, and direct agglutination test. A diagnosis of recent acute acquired infection is confirmed if there is a serial twotube rise in titer when serums drawn at 3-week intervals are run at the same time or if there is a serial twotube rise in titer when serums drawn at 3-week intervals are run at the same time or if there is a seroconversion from a negative to a positive titer. A single high titer in any test does not prove the presence of active infection because of the presistent levels of IgG antibodies that occur in chronic infections. It is also possible to specifically test for the presence of IgM antibodies to diagnose early acute stage infection. However, current techniques that rely on the detection of IgM Toxoplasma antibodies require a step of distinquishing IgM antibodies from IgG antibodies, which complicates detection of the acute stage. In addition, IgM antibody levels can remain high in some cases of chronic infection for a year or more. A publication has recently reported a difference in agglutination of acetone-treated Toxoplasma parasites by patient sera as opposed to agglutination of formalin-treated parasites. However, comparison of titers of the two agglutinations is required for practical diagnosis of the stage of Toxoplasma infection.

Accordingly, simplified techniques that enable detection of the acute stage of Toxoplasma infection are needed.

SUMMARY OF THE INVENTION

The present invention provides a method of detecting Toxoplasma infection and distinguishing acute infection from chronic infection comprising the steps of combining a sample suspected of containing antibodies to Toxoplasma antigens with an acute-phase-specific Toxoplasma antigen under conditions favorable for formation of antigen-antibody complex and detecting formation of the complex. An individual acute-phases-pecific antigen can be either an acetone-treated (AC) tachyzoite antigen or an unmodified tachyzoite antigen specifically reactive with an antibody to an AC antigen. In contrast to prior teachings, it has been determined that the specificity of antibodies, including IgG antibodies, differs in acute and chronic stages of Toxoplasma infection, with antibodies reactive with acetonetreated Toxoplasma antigens (or equivalent unmodified antigens) being diagnostic of acute Toxoplasma infection without requiring a comparison to antisera of the same patient reacting with other antigen formulations. The unmodified tachyzoite-specific antigens can be isolated and purified using antibodies reactive with acetone-treated Toxoplasma antigens.

BRIEF DESCRIPTION OF DRAWINGS

This invention will be better understood by reference to the following detailed description of specific embodiments when considered in combination with the drawings that form part of this specification, wherein:

FIG. 1 is a photograph of immunoblots used to define and compare Toxoplasma antigens recognized by the acute and chronic phase sera of human patients.

FIG. 2 is a photograph showing immunoblots of unmodified Toxoplasma antigens labeled with different antisera.

DETAILED DESCRIPTION OF SPECIFIC EMBODIMENTS

Figure 3A:
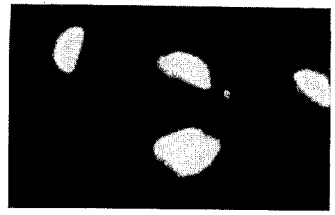
FIG. 3 is a series of four photographs showing immunofluorescent labeling of tachyzoites or bradyzoites with different antibody preparations.

Investigations leading to the present invention have indicated that an agglutination test for IgG Toxoplasma antibodies using acetone-treated antigens from the tachyzoite stage of Toxoplasma gondii (AC antigens) can be judged as being positive using sera from patients during the acute stage of their infection in a single agglutination assay. In contrast, when the same assay is carried out with formalin-treated tachyzoite antigens (HS antigens), agglutination occurs during both the acute and chronic (latent) stages of infection.

Specific unmodified antigens (tachyzoite-specific, acute-phase-specific antigens) have been defined by the investigations. "Unmodified" is used here to indicate that the original antigens have been isolated using techniques that do not disrupt covalent bonds that would be present in a glycoprotein or introduce new bonds into such molecules. The term unmodified is also being used to indicate a potential difference between the purified natural antigens and antigens treated with acetone. It should be recognized that the acetone-treated antigens may or may not have covalent bonds different from those present in the corresponding unmodified antigens. It is not known whether the acetone is acting as a fixative to cause protein crosslinking or merely acts to solublize and/or denature various proteins to either bring certain proteins into solution or remove other proteins from the solution or suspension being purified. Additionally, it is possible that acetone is acting on the membrane to expose a portion of the molecule not previously exposed. Absolute knowledge of the true nature of the antigens, however, is not necessary for the practice of the invention since the techniques described herein can be used to distinguish acute-phase from chronic-phase Toxoplasma infection without reference to the theory by which the system operates.

Sera from individuals with acute but not chronic infection reacted strongly with ten unmodified antigens that were also recognized by antiserum of mice immunized with AC antigens. These acute-phase-specific unmodified and AC antigens were therefore diagnostic for the tachyzoite (acute infection) stage of $T.$ $gondii.$ Antibodies directed to AC antigens (AC antibodies) reacted with the cell membrane of tachyzoites but not with the cell membrane of bradyzoites (chronic stage), whereas HS antibodies reacted with cell membranes of both forms of the organism in an immunofluorescence test. Accordingly, the acute-phase-specific antigens of the invention are useful for differentiating between the acute and chronic stages of Toxoplasma infection through their detection by IgG or IgM antibodies. Additionally, AC antibodies can be used for direct detection of antigens indicative of acute-phase infection.

It will be apparent, therefore, that an "acutephase-specific antigen reactive with an antibody specific for an acetone-treated Toxoplasma antigen" can be either an acetone-treated Toxoplasma antigen itself or an unmodified Toxoplasma antigen obtained from a tachyzoite that reacts specifically with such an antibody (i.e., the antibody binds to the antigen at the specific binding site of the antibody). By specific binding is meant a ratio of tachyzoite to bradyzoite binding affinities, for any particular antibody, of at least 10, preferably at least 100, and more preferably at least $10^3$ (tachyzoite binding affinity divided by bradyzoite binding affinity). Affinity here can mean either monovalent binding affinity or the binding affinity associated with divalent binding of antibodies, often referred to as avidity. However, comparisons should be made with like types of binding affinity (avidity with avidity or monovalent affinity with monovalent affinity).

As will be apparent from the following description, it is not clear whether an "AC antigen" is in fact different from an "HS antigen" or merely represents a different part of the same molecule; i.e., a different epitope on the same molecule. Additionally, the 10 antigens indicated above may represent subunits or aggregations of molecules as they exist in their natural state. However, as indicated above, the theoretical underpinnings need not be completely set forth as the following description allows practice of the invention without reference to theory.

AC antigens are prepared from the tachyzoite stage of any strain of T. gondii, particularly the RH strain. For example, tachyzoites can be harvested from peritoneal fluids of mice infected 2 days earlier and can be purified by any convenient procedure, such as that described in Wilson et al., *J. Exp. Med.* (1980) 151:328-346. Generally, whole tachyzoites are used to prepare AC antigens. The tachyzoites are washed by centrifugation and suspended in a buffer of pH 6.8 to 8.0, preferably about 7.2. Phosphate-buffered saline (PBS) is a preferred buffering medium, although other buffers can be used. The suspended tachyzoites are acetone-treated by addition of sufficient acetone to provide a final concentration of from 15-35, preferably about 25% at 0°-10° C., preferably about 4° C. for 48-96 hours, preferably about 72 hours. As is well understood to those skilled in the art, concentration of acetone, temperature, and time of fixation can be varied within the limits described to obtain equivalent results. For example, satisfactory results can be obtained by treatment with 30% acetone in PBS pH 7.2 at 4° C. for 72 hours. Additionally, it is possible to replace acetone with methanol to achieve equivalent results. Acetone and methanol treatments are similar, differing principally in the length of treatment, which normally ranges from 24-48 hours, preferably about 36 hours. Other limits as set forth above for acetone treatment produce satisfactory results for methanol treatment.

In addition to whole organisms, membrane fractions of tachyzoites can also be used. For example, membranes can be isolated (e.g., as a sonicated suspension) or attached to solid surfaces for use in preparation of AC antigens. Any other treatment that provides cell membranes with unmodified surface proteins can also be used.

It will be recognized that any of the individual limits set forth to specify a range can be selected individually as upper and lower limits to provide a series of ranges of intermediate preference. For example, upper and lower concentration limits of 15 and 25% acetone can be selected to provide a concentration range of intermediate preference.

The AC antigens can be used to prepare antisera or monoclonal antibodies that can be used in diagnostic tests or to obtain or identify acute-phasespecific, unmodified *T. gondii* antigens, or any other antigens, whether modified in the same or a different manner, that have the antigenic specificity of AC antigens. Any of the known techniques of preparing antisera and/or monoclonal antibodies can be used. For example, a vertebrate, particularly a mammal, more particularly a rodent (e.g., mouse or rat), can be immunized by the intraperitoneal route using standard techniques. An exemplary immunization protocol comprises injecting twice 4 weeks apart with an antigenic preparation containing approximately $1.5 \times 10^{10}$ AC-treated cells (using mice). Serum can be obtained from blood of the immunized animal after completion of the immunization protocol. For example, blood for the preparation of antisera can be collected approximately one week after the second immunization described above when mice are used as the immunized species. Typical techniques for preparing monoclonal antibodies are described in, for example, U.S. Pat. No. 4,381,292. These techniques can be used to prepare AC monoclonal antibodies by replacing the immunogens described therein with AC antigen preparations of this invention.

Antibodies produced by hybridomas or present in antisera can be purified by any convenient technique, such as chromatography, electrophoresis, precipitation, extraction, or the like. Antibodies specific for AC antigens can be employed without further change after purification or can be modified by reduction to various fragments, such as F(ab')$_2$, Fab, Fb, and the like.

Monoclonal antibodies or antisera that bind specifically with AC antigens can be used to isolate unmodified antigens specifically associated with the tachyzoite stage of T. gondii, as described above. Such purifications are conveniently carried out in an affinity column using standard techniques for attaching the antibodies as described herein to the column material. Techniques for attaching antibodies to solid surfaces are well known and are described in numerous patents and publications, such as U.S. Pat. Nos. 4,376,110 and 4,486,530 (which describe techniques in which monoclonal antibodies are attached to solid surfaces).

AC antigens, antibodies against AC antigens, and unmodified acute-phase-specific antigens identified by such antibodies can be used in a wide variety of diagnostic assays as well as for other purposes. Diagnostic tests can be carried out in which the analyte is either T. gondii itself or an antibody to T. gondii in the serum or plasma of the infected host, typically a human patient but possibly also a host animal of another species, such as a sheep, pig, dog, cat, or the like. Tests for T. gondii antigens can also be carried out on other bodily fluids or on tissues, such as peritoneal fluid, cerebrospinal fluid, urine, and biopsy samples. For diagnostic tests, the AC antigens or the purified acute-phase-specific antigens can be used as standards or as reactants for determining the presence of antibodies synthesized by the host against an T. gondii infection. The various antibody preparations (monoclonal, polyclonal, or antiserza) can be used to detect the presence of T. gondii infections by direct analysis for the infective organism or antigens therefrom. A wide variety of diagnostic assays, either competitive or non-competitive are described in the literature using a variety of detectable labels. Such labels include radioisotopes, enzymes, particles (e.g., magnetic particles, glass particles, latex particles, or carbon particles), fluorescent molecules (e.g., fluorescein, umbelliferone, phycobiliproteins, or rhodamine), chemiluminescers, enzyme substrates, co-factor inhibitors, or the like. Illustrative references describing various techniques include U.S. Pat. Nos. 3,654,090, 3,817,837, 3,935,094, 4,134,792, 4,160,645, 4,192,983, 4,208,479, 4,275,149, and 4,341,865. The manner of attachment of an antibody or antigen to the label is conventional, there being a wide variety of techniques described in the literature cited above.

For diagnosis, antibodies and antigens can be provided in kits, wherein the antibodies or antigens are included with other reagents necessary for the analytical determination. Particularly, for enzyme assays, the other reagents would include necessary substrates and co-factors, protein stabilizers, buffers, salts, biocides, and the like. Similarly, reagents could be provided in kit form for any of the assays described herein or in the cited publications.

In addition to use in diagnostic assays, specific antigens and antibodies thereto can be used for other purposes. For example, the antigens can be used to prepare monoclonal antibodies as described herein. Monoclonal antibodies can be used to prepare anti-idiotypic antibodies, which can be used as analyte mimics or as immunogens. Additionally, the acute-phase-specific antigens can be used as immunogens in the preparation of vaccines, or the antibodies specific for these antigens can be used as passive vaccines.

Twelve specific membrane antigens have been identified as being acute-phase-specific. Ten antigens were identified by using sera of mice immunized with AC antigens in an immunoblot analysis. Sera from individuals with acute but not chronic infection reacted strongly with these same ten antigens in immunoblots. Approximate molecular weights of the acute-phase-specific antigens recognized by mouse anti-AC antibodies are 116,000, 78,000, 64,000, 61,000, 54,000, 52,000, 42,000, 30,000, 24,000, and 6,000 as measured by gel electrophoresis. Rabbit antisera identifies two additional acute-phase-specific antigens of 48,000 and 32,000 molecular weight.

It is somewhat surprising that antibodies prepared against AC antigens can be used in affinity chromatography to isolate antigens that are specific for the tachyzoite stage of T. gondii. Prior evidence had indicated that the AC antigens and HS antigens shared epitopes and might be part of the same molecules. However, it has been determined that the twelve antigens discussed above (or at least specific epitopes on these antigens) are specific for the identification of the tachyzoite stage of T. gondii and do not suffer from cross-reactivity with the intact bradyzoite stage.

The invention now being generally described, the same will be better understood by reference to the following examples which are provided for purposes of illustration and are not to be considered limiting of the invention unless so specified.

EXAMPLES

A series of experiments were carried out to characterize the antigens associated with acute-phase toxoplasmosis.

Materials and Methods

Mice. Outbred female Swiss-Webster mice (Simonsen Laboratories, Gilroy, CA) were 6 to 8 weeks old when used in the experiments.

Human sera. Sera were obtained from more than 20 adult patients who had acute lymphadenopathic toxoplasmosis. Diagnosis of acute lymphadenopathic toxoplasmosis was by both serology and histopathology.

Toxoplasma antigens. Tachyzoites of the RH strain were harvested from peritoneal fluids of mice infected 2 days earlier and purified as described in Welson et al., *J.*

*Exp. Med.* (1980) 151:328–346. For the agglutination test, tachyzoites were fixed with either formalin (HS antigen) or acetone (AC antigen) as described in Thulliez et al., *Pathol. Biol.* (1986) 34: 173–177. In brief, tachyzoites were washed by centrifugation and suspended in phosphate-buffered saline pH 7.2 (PBS). For acetone fixation, they were treated with 30% acetone in PBS at 4° C. for 72 hrs. For formalin fixation, tachyzoites were suspended in 20% formalin in PBS overnight.

Gel electrophoresis and immunoblotting. Electrophoresis was performed in 5 to 15% acrylamide slab gels with the discontinuous sodium dodecyl sulfate (SDS) buffer system described in Laemilli, *Nature* (1970) 227: 680–685. Fresh (not fixed in acetone or formalin) tachyzoites were solubilized in the sample SDS buffer described in the Laemelli publication, which is (per liter) 7.57 g Trizma base, 100 g glycerol, 23 g sodium dodecyl sulfate, and 7.7 g dithiothreitol. Molecular weight standards were myosin, $\beta$-galactosidase, phosphorylase B, bovine serum albumin, egg albumin, and carbonic anhydrase (Sigma, St. Louis, MO). Proteins separated by electrophoresis were transferred to nitrocellulose papaer as described by Towbin et al., *Proc. Natl. Acad. Sci. USA* (1979) 76:4350–4354. Blots were first soaked in 5% nonfat dried milk in PBS for 1 hr at room temperature to saturate unused protein binding sites. The blots were then rinsed in TBS containing 0.05% Tween 20 (PBS-Tween) and incubated overnight with test serum at a 1/100 dilution in 5% dried milk in PBSTween. The nitrocellulose sheets were then washed with PBS-Tween and incubated for 1 hr at room temperature with horseradish-peroxidase-conjugated goat anti-human IgG or anti-mouse IgG antibodies (Tago Inc., Burlingame, CA) at dilutions emperically determined to be optimum. After another wash, blots were soaked in a solution of 0.1 mg/ml of diaminobenzidine and 0.1% $H_2O_2$ in PBS. Color development was stopped by washing with PBS-Tween.

Toxoplasma serology. IgG antibodies were measured in the Sabin-Feldman dye test (Sabin and Feldman, *Science* (1948) 108:660–663) and IgM antibodies in the DS-IgM-ELISA as described previously (Naot and Remington, *J. Infect Dis.* (1980) 142:757–766).

The agglutination tests using HS (HS test) or AC antigens (AC test) were performed as follows. In brief, HS antigen was suspended in PBS at a concentration of $3 \times 10^7$ tachyzoites/ml. Fifty $\mu$l of the suspension was added to 50 $\mu$l of doubling dilutions of sera in microtiter plates. Sera were diluted in PBS containing 0.2 M 2-mercaptoethanol. The trays were incubated at room temperature overnight, and the agglutination patterns were then read. AC antigen was suspended in alkaline buffer (pH 8.7) containing 1% bovine serum albumin. The concentration of tachyzoites was the same as for HS antigen. Sera were diluted in the same buffer containing 0.2 M 2-mercaptoethanol. Toxoplasma antibody titers in the dye and aggultination tests were expressed in International Units (IU)/ml for both human and mouse sera. The relationship between titers expressed as the reciprocal of the dilutions and IU in each test was determined by use of the World Health Organization standard serum which contains 2000 IU/vial.

IFA test. The IFA test was performed using either tachyzoites or bradyzoites as described for tachyzoites by Walton et al., *Am. J. Trop. Med.* (1966) 15:149–152. Cysts of *T. gondii* were purified by Percol density gradient centrifugation from brains of mice chronically infected with the ME49 strain. Free bradyzoites were obtained by treatment of cysts with pepsin. The bradyzoites were fixed in 2% formalin in PBS and attached to the surface of glass slides by drying the suspension on the slides. Separate slides were coated with formalin-treated tachyzoites. The slides were incubated at 37° C. for 1 hr with dilutions of the test sera. After washing, slides were incubated with a 1:50 dilution of FITC-conjugated goat anti-mouse IgG (Cappel, Cochranville, Pa.) for 1 hr at 37° C.

Preparation of antisera against AC and HS antigens. Mice were immunized by the intraperitoneal route with AC or HS antigens. Each antigen preparation contained $1.5 \times 10^7$ cells. The mice were injected twice four weeks apart. They were sacrificed, and pooled sera were obtained one week after the second immunization.

Absorption of AC antibodies with HS antigens. Three hundred microliters of a 1:10 dilution of the AC antisera in PBS were incubated with $4.5 \times 10^7$ cells of HS antigens at 37° C. for 1 hr. After incubation, HS antigens were removed by centrifugation at $1300 \times G$ for 10 min. Repeat absorptions were performed to attempt to remove reactive antibodies.

Results

Sera of patients with acute lymphadenopathic toxoplasmosis. Table 1 shows the serological test results from a number of techniques obtained in sera from five representative patients from whom serum was obtained both during the acute stage of their toxoplasmic lymphadenopathy and later during their chronic (latent) infection. The first four patients were immunocompromixed. All five patients were diagnosed clinically prior to serological testing. The high IgG (dye test) and IgM test titers are characteristic of the acutephase of toxoplasmic lympadenopathy. However, note the high titers in the chronic stage for Patient 5.

The agglutination test used whole, fixed organisms as described in Thulliez et al., *Path. Biol.*(1986) 34:173–177. This test is described in the cited literature as requiring a comparison between HS and AC titers in order to verify a diagnosis of acute-stage infection.

TABLE 1

Toxoplasma Antibody Titers in Sera of Patients in the Acute and the Chronic Stage of the Infection

| Patient | Date | Stage of Infection | Anti-Toxoplasma Antibody Titers | | | |
|---|---|---|---|---|---|---|
| | | | | | Agglutination Test[1] | |
| | | | IgM-ELISA[2] | Dye Test[3] | AC[3,4] | HS[3,4] |
| 1 | 01/20/75 | acute | 12.4 | 1,600 | 1,600 | 3,200 |
| | 03/27/78 | chronic | 3.9 | 819 | <100 | 400 |
| 2 | 09/23/76 | acute | 3.6 | 2,400 | 400 | 1,600 |
| | 10/07/80 | chronic | 0.6 | 410 | <100 | 200 |
| 3 | 04/14/76 | acute | 4.8 | 3,200 | 400 | 1,600 |
| | 02/24/78 | chronic | 0.6 | 26 | <100 | 400 |
| 4 | 05/26/81 | acute | 10.6 | 4,000 | 800 | 1,600 |

TABLE 1-continued

Toxoplasma Antibody Titers in Sera of Patients
in the Acute and the Chronic Stage of the Infection

| Patient | Date | Stage of Infection | Anti-Toxoplasma Antibody Titers | | | |
|---|---|---|---|---|---|---|
| | | | IgM-ELISA[2] | Dye Test[3] | Agglutination Test[1] | |
| | | | | | AC[3,4] | HS[3,4] |
| | 02/01/83 | chronic | 4.3 | 179 | <100 | 800 |
| 5 | 09/28/81 | acute | 12.0 | 2,400 | 400 | 800 |
| | 02/20/82 | chronic | 6.0 | 12,800 | <100 | 6,400 |

[1]This agglutination test uses whole fixed organisms, not isolated antigens.
[2]Expressed as described by Siegel and Remington, J. Clin. Microbiol. (1983) 18:63-70.
[3]Expressed as IU/ml.
[4]Positive determined by AC/HS ratio.

IgG-ELISA test employing purified unmodified AC antigens. Purified, unmodified acute-stage-specific antigens were obtained from tachyzoites using affinity chromatography. Preparation of toxoplasma antigens and of antisera against AC antigens are described above. Immulon I plates were coated with the purified antigens in 0.1 M carbonate buffer, pH 9.8. After post-coating the plates with a solution of bovine serum albumin, the plates were incubated with patient sera diluted in phosphate-buffered saline (pH 7.2). Thereafter, the plates were incubated with horseradish-peroxidase-labeled antihuman IgG antibody. Absorbance at 490 nm was measured after 10 minutes incubation with a solution of 0-phenylenediamine, a substrate for the peroxidase.

Results of this assay, referred to as an AC-IgG-ELISA assay, are compared to other serological tests on serial sera from toxoplasmic lymphadenopathy patients in Table 2 below.

TABLE 2

Comparison of Results Between AC-IgG ELISA Test and Other Serological Tests on Serial Sera from Toxoplasmic Lymphadenopathy Patients

| Patient | Duration of Lymphadenopathy | Toxoplasma Serological Test Titers[1] | | | | |
|---|---|---|---|---|---|---|
| | | IgM-ELISA | Dye Test | Agglutination Test | | AC-IgG-ELISA[2] |
| | | | | AC | HS | |
| 1 | 1 week | 0.5 | <16 | <100 | <100 | 12 |
| | 3 week | 11.5 | 1024 | ≧1600 | 100 | 16 |
| | 1.5 M | 12.8 | 2048 | ≧1600 | 200 | 14 |
| | 3 M | 10.1 | 512 | 200 | 400 | 3 |
| | 4 M | 7.7 | 2048 | 400 | 1600 | 9 |
| 2 | 1 M | 3.2 | 8000 | ≧1600 | 200 | 46 |
| | 5 M | 1.2 | 8000 | 200 | 100 | 10 |
| | 14 M | 1.2 | 8000 | <100 | 800 | 4 |
| | 50 M | 0.6 | 8000 | <100 | 200 | 6 |
| 3 | 2 M | 4.1 | 32000 | 400 | 1600 | 10 |
| | 7 M | 1.6 | 2048 | <100 | 3200 | 7 |
| | 24 M | 0.6 | 128 | <100 | 400 | 5 |
| 4 | 1 M | 10.6 | 8000 | 800 | 1600 | 185 |
| | 22 M | 4.3 | 512 | <100 | 800 | 7 |
| 5 | 1 M | 6.4 | 4096 | 200 | 800 | 14 |
| | 20 M | 0.4 | 256 | <100 | <100 | 8 |

[1]See Table 1 for IgM-ELISA, Dye Test, and AC/HS Agglutination Test.
[2]Titer = O.D. × 1000; Titer ≧10 is positive for acute-stage infection.

As seen from the results expressed in Table 2, the IgM-ELISA, dye test, and agglutination test all failed to detect acute-stage infection in the first week for Patient 1. The AC-IgG-ELISA test, on the other hand, using purified antigens as described for the present invention, was capable of diagnosing acute-stage infection at this time. Additionally, the test of the invention unequivocally distinguished acute-stage from chronic-stage infection at all times for all patients in contrast to any single diagnosis of the prior tests, including the whole acetone-treated organisms used in the agglutination test.

Toxoplasma antigens recognized by antibodies formed during the acute and chronic stages of the infection. Immunoblots were used to define and compare Toxoplasma antigens recognized by the acute and chronic phase sera of the patients shown in Table 1. An SDS lysate of tachyzoites was used as the antigen for these studies. As shown in FIG. 1, acute phase sera recognized more antigens than did chronic phase sera, and certain bands were present in only the former or were more strongly stained in those bolts.

Antigens recognized by anti-AC and anti-HS antibodies. To identify antigens unique to AC and HS antigens, mice were immunized with either AC or HS antigens to prepare antisera for testing by immunoblot. The AC and HS test titers of these antisera are shown in Table 3. Antisera from mice immunized with either antigen preparation had high antibody titers in both AC and HS tests. This indicates that AC and HS antigens share some of the same determinants.

TABLE 3

AC and HS Agglutination Test Titers in Sera of Mice Immunized with either the AC or HS Antigen Preparation

| Antiserum | Agglutination Test Titers* | |
|---|---|---|
| | AC | HS |
| AC | 3,200 | 3,200 |
| HS | 1,600 | 12,800 |

*IU/ml

Toxoplasma antigens recognized by the antisera prepared against AC and HS antigens were analyzed by immunoblotting using the SCS Toxoplasma lysate antigen preparation. As shown in FIG. 2, the AC antisera recognized fewer numbers of antigens than did the HS antisera. Approximate molecular weights of the most prominently stained bands recognized by the AC antibodies were 116,000, 78,000, 64,000, 61,000, 54,000, 52,000, 42,000, 30,000, 24,000, and 6,000. Antigens with comparable molecular weights to these ten were more intensely stained when reacted with the acute-phase human sera than when reacted with the chronic phase sera (arrows in FIG. 1), but not all were recognized by all of the acute sera.

All bands in the bolts obtained with the AC antibodies were present in blots obtained with the HS antibodies. Additional antigens were present in the blots treated with HS antibodies which were not present in the bolts treated with AC antibodies (FIG. 2).

Absorption of AC antibodies with HS antigens. Because the results described abvoe suggest that AC antigens are a part of HS antigens, absorption studies were performed to determine whether HS antigens could remove the mouse AC antibodies. FIG. 3a shows that AC antibodies reacted with only cell membranes of HS antigens. Changes in the AC and HS agglutination test titers when the AC antibody preparation was used following each of several absorptions with HS antigens are shown in Table 4. Both the AC and HS test titers decreased and ultimately were undetectable.

TABLE 4

Results of Absorption of Mouse AC Antibodies with HS Antigens

| Number Absorptions | Agglutination Test Titers* | |
|---|---|---|
|  | AC | HS |
| 0 | 1,600 | 800 |
| 1 | 400 | 400 |
| 2 | 100 | 100 |
| 3 | 50 | 50 |
| 4 | <50 | <50 |

*IU/ml

Following the final absorption, immunoblots were performed with these absorbed antisera. All but one (M.W. 116,000) of the bands recognized by the AC antibodies disappeared after the absorption. The intensity of the band was much weaker than before absorption.

Figure 3B:
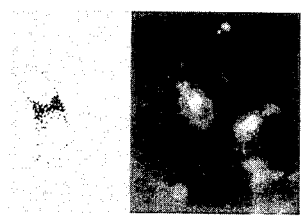
Figure 3C:
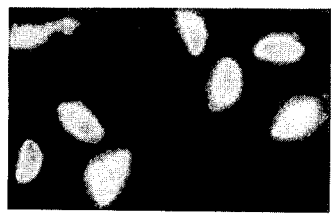
Figure 3D:
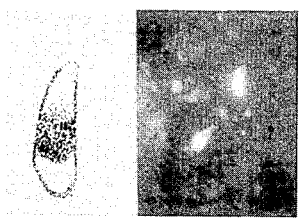

Reaction of AC and HS antibodies with tachyzoites and bradyzoites. Reactivities of AC and HS antibodies with tachyzoites and bradyzoites were examined by the IFA test using formalin-treated organisms. HS antibodies recognized the cell membranes of both the tachyzoites and bradyzoites (FIGS. 3c and 3d). In contrast, AC antibodies reacted with cell membranes of only tachyzoites (FIGS. 3a and 3b). Normal mouse sera did not give a positive reaction with either form. A bright spot was noted in the center of the bradyzoites when they were incubated with either AC or HS antibodies.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of detecting toxoplasma infection and distinguishing acute infection from chronic infection, comprising:

combining (1) a sample suspected of containing antibodies to toxoplasma antigens with (2) an acute-phase-specific toxoplasma antigen reactive with an antibody specific for an actone-treated acute-phase-specific toxoplasma antigen, wherein said combining occurs under conditions favorable for formation of antigen-antibody complex; and detecting formation of a complex between IgG antibodies in said sample and said acute-phase-specific toxoplasma antigen as being diagnostic of acute infection.

2. The method of claim 1, wherein said acute-phase-specific toxoplasma antigen is a cell-surface antigen.

3. The method of claim 1, wherein said acute-phase-specific toxoplasma antigen is a cytoplasma antigen.

4. The method of claim 1, wherein said acute-phase-specific toxoplasma antigen has a molecular weight of approximately 116,000, 78,000, 64,000, 61,000, 54,000, 52,000, 48,000, 42,000, 32,000, 30,000, 24,000, or 6,000 as measured by sodium dodecyl sulfate polyacrylamide gel electrophoresis.

5. The method of claim 1, wherein said acetone-treated antigen comprises a tachyzoite cell-surface antigen contacted with acetone in aqueous solution.

6. The method of claim 1, wherein said acetone-treated antigen is obtained by contacting a tachyzoite cell membrane with 15–35% acetone at 0°–10° C. for 48–96 hours in an aqueous solution buffered at pH 6.8 to 8.0.

7. The method of claim 6, wherein said cell membrane is contacted with 25% acetone in phosphate buffer at a pH of about 7.2 for about 72 hours at about 4° C.

8. The method of claim 1, wherein said acute-stage-specific antigen obtained by contacting a tachyzoite cell membrane with methanol in an aqueous buffer.

9. The method of claim 1, wherein a diagnostic determination of acute infection is carried out without detecing complex formation between said antibodies in said sample and formalin-treated toxoplasma antigens.

10. A method of detecting antibodies in a sample, wherein antibodies are specific for at least one acetone-treated toxoplasma cell-surface antigen associated with tachyzoites, said antibodies being less strongly bound to cell-surface antigens of bradyzoites.

11. The method of claim 10, wherein said method is carried out without analyzing said sample for anti-toxoplasma antibodies specific for formalin-treated toxoplasma cell-surface antigens associated with tachyzoites.

* * * * *